(12) United States Patent
Kim

(10) Patent No.: US 10,432,180 B2
(45) Date of Patent: Oct. 1, 2019

(54) APPARATUS AND METHOD FOR SIGNAL PROCESSING BY CONVERTING AMPLIFIED DIFFERENCE SIGNAL

(71) Applicant: Samsung Electronics Co., Ltd., Suwon-si (KR)

(72) Inventor: JongPal Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/161,329

(22) Filed: Oct. 16, 2018

(65) Prior Publication Data
US 2019/0052251 A1 Feb. 14, 2019

Related U.S. Application Data

(62) Division of application No. 15/158,001, filed on May 18, 2016, now Pat. No. 10,141,918.

(30) Foreign Application Priority Data

Nov. 4, 2015 (KR) .................. 10-2015-0154351

(51) Int. Cl.
*H04N 5/18* (2006.01)
*H03K 5/003* (2006.01)
(Continued)

(52) U.S. Cl.
CPC ......... *H03K 5/003* (2013.01); *A61B 5/04004* (2013.01); *A61B 5/0428* (2013.01);
(Continued)

(58) Field of Classification Search
CPC .............. A61B 5/04004; A61B 5/0428; A61B 5/04288; A61B 5/7225; G11C 27/024; G11C 27/026; H03K 5/003
See application file for complete search history.

(56) References Cited

U.S. PATENT DOCUMENTS

| 4,467,813 A | 8/1984 | Schomburg |
| 4,641,105 A | 2/1987 | Albaugh et al. |

(Continued)

FOREIGN PATENT DOCUMENTS

| EP | 0857372 A1 | 8/1998 |
| JP | 2008-211808 A | 9/2008 |

(Continued)

OTHER PUBLICATIONS

Extended European Search Report dated Aug. 14, 2017 in corresponding European Patent Application No. 16183655.6 (13 pages in English).

(Continued)

*Primary Examiner* — Kenneth B Wells
(74) *Attorney, Agent, or Firm* — NSIP Law

(57) ABSTRACT

A signal processing apparatus includes: a difference signal acquirer configured to obtain a difference signal reflecting a change in an input signal at a preset time interval based on a reference signal; a signal amplifier configured to amplify the difference signal; and a signal restorer configured to generate an output signal by converting the amplified difference signal to a digital signal and summing the digital signal.

11 Claims, 14 Drawing Sheets

(51) Int. Cl.
    *A61B 5/04*         (2006.01)
    *A61B 5/0428*     (2006.01)
    *G11C 27/02*      (2006.01)
    *H03F 3/45*       (2006.01)
    *A61B 5/00*       (2006.01)
    *H03M 3/02*      (2006.01)
    *H03M 1/12*      (2006.01)

(52) U.S. Cl.
    CPC ........ *A61B 5/04288* (2013.01); *A61B 5/7225* (2013.01); *G11C 27/024* (2013.01); *G11C 27/026* (2013.01); *H03F 3/45475* (2013.01); *H03M 3/02* (2013.01); *A61B 2560/0209* (2013.01); *H03F 2200/261* (2013.01); *H03F 2203/45428* (2013.01); *H03F 2203/45551* (2013.01); *H03M 1/124* (2013.01)

(56) References Cited

U.S. PATENT DOCUMENTS

| | | | |
|---|---|---|---|
| 4,859,871 A | 8/1989 | Kobayashi et al. | |
| 5,715,049 A | 2/1998 | Ohsuka et al. | |
| 6,377,200 B1 * | 4/2002 | Lee | H03M 1/1215 341/155 |
| 6,496,128 B2 | 12/2002 | Wiesbauer et al. | |
| 6,553,131 B1 | 4/2003 | Neubauer et al. | |
| 7,034,737 B1 * | 4/2006 | Huang | H03M 1/147 341/144 |
| 7,747,070 B2 | 6/2010 | Puri | |
| 8,120,423 B2 * | 2/2012 | Deng | H03F 3/45 327/124 |
| 8,350,736 B2 * | 1/2013 | Chern | H03M 1/1019 324/142 |
| 8,384,806 B2 | 2/2013 | Robinson et al. | |
| 10,141,918 B2 * | 11/2018 | Kim | H03K 5/003 |
| 2010/0033240 A1 | 2/2010 | Denison et al. | |
| 2010/0308907 A1 | 12/2010 | Xiang et al. | |
| 2011/0169921 A1 | 7/2011 | Lee et al. | |
| 2013/0113553 A1 | 5/2013 | Hsieh | |
| 2013/0251271 A1 | 9/2013 | Li | |
| 2015/0002221 A1 | 1/2015 | Van Helleputte et al. | |
| 2015/0200637 A1 | 7/2015 | Ko et al. | |

FOREIGN PATENT DOCUMENTS

| | | |
|---|---|---|
| KR | 10-0927234 B1 | 11/2009 |
| KR | 10-1025405 B1 | 3/2011 |
| KR | 10-1360648 B1 | 2/2014 |

OTHER PUBLICATIONS

Partial European Search Report dated Mar. 29, 2017, in counterpart European Application No. 16183655.6 (6 pages, in English).

* cited by examiner

100

APPARATUS AND METHOD FOR SIGNAL PROCESSING BY CONVERTING AMPLIFIED DIFFERENCE SIGNAL

CROSS-REFERENCE TO RELATED APPLICATIONS

This application is a divisional of U.S. patent application Ser. No. 15/158,001 filed on May 18, 2016 which has now issued as U.S. Pat. No. 10,141,918, and which claims the benefit under 35 USC 119(a) of Korean Patent Application No. 10-2015-0154351 filed on Nov. 4, 2015, in the Korean Intellectual Property Office, the entire disclosures of which are incorporated herein by reference for all purposes.

BACKGROUND

1. Field

The following description relates to signal processing technology.

2. Description of Related Art

An instrumentation amplifier (IA) is used to measure various types of signals. For example, in a medical field, the IA is used to measure and amplify a biosignal such as an electrocardiogram (ECG), an electromyogram (EMG), a photoplethysmogram (PPG), a body resistance, and a motion signal. In general, the IA may be configured as a differential amplifier having a low offset, low noise, high common-mode rejection, high loop gain, and high input resistance. For example, such a differential amplifier may amplify an input signal within a circuit operation range and output the amplified signal.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

According to one general aspect, a signal processing apparatus includes: a difference signal acquirer configured to obtain a difference signal reflecting a change in an input signal at a preset time interval based on a reference signal; a signal amplifier configured to amplify the difference signal; and a signal restorer configured to generate an output signal by converting the amplified difference signal to a digital signal and summing the digital signal.

The difference signal acquirer may include a first switch configured to be controlled by a first control signal, and the first switch may be configured to generate the difference signal by periodically connecting an input terminal of the signal amplifier to a reference signal based on the first control signal, and periodically connecting the input terminal of the signal amplifier to the input signal.

The input terminal of the signal amplifier may be reset to be the reference signal in response to the first switch being controlled to be in a closed-circuit state by the first control signal. The input signal may be input to the input terminal of the signal amplifier in response to the first switch being controlled to be in an open-circuit state by the first control signal.

The first control signal may be configured to control the first switch to perform a switching operation with respect to the input signal in a period shorter than a period of the input signal.

The incremental summing of the digital signal may include summing the digital signal corresponding to a period of the input signal.

A signal amplitude range of the difference signal may be smaller than a signal amplitude range of the input signal.

The signal processing apparatus may further include a switch configured to generate the difference signal by periodically connecting an input terminal of the signal amplifier to the reference signal, and periodically connecting an input terminal of the signal amplifier to the input signal.

The difference signal acquirer may further include a first capacitor to which the input signal is input, and a terminal of the first switch, a terminal of the first capacitor, and the input terminal of the signal amplifier may be electrically connected to one another.

The difference signal may reflect repeated changes in the input signal at a preset time interval through repeated switching operations.

The signal restorer may include: a sampler and holder configured to sample the amplified difference signal to generate a sampled signal, and hold the sampled signal; a signal converter configured to convert the sampled signal to the digital signal; and a signal adder configured to generate the output signal by summing the digital signal.

The sampler and holder may be configured to sample the amplified difference signal at a point in time after a previous closed-circuit switching operation and before a switch performing the switching operation is closed-circuited.

The signal restorer may further include a filter configured to perform low-pass filtering on the sampled signal, and the signal converter may be configured to convert, to the digital signal, a signal obtained through the low-pass filtering.

According to another general aspect, signal processing method includes: obtaining a difference signal of an input signal based on a switching operation applied to the input signal; amplifying the difference signal; converting the amplified difference signal to a digital signal; and generating an output signal by summing the digital signal to restore a signal representing an amplification of the input signal.

According to another general aspect, a signal processing apparatus includes: a signal amplifier comprising a first input terminal, a second input terminal, a third input terminal and a fourth input terminal; a first inputter configured to transfer a first input signal alternately to the first input terminal and the second input terminal; and a second inputter configured to transfer a second input signal alternately to the third input terminal and the fourth input terminal, wherein the signal amplifier is configured to amplify a difference signal based on the first input signal and the second input signal, and output the amplified difference signal.

The apparatus first inputter may include: a first switch of which a switching operation is controllable based on a first control signal; and a second switch of which a switching operation is controllable based on a second control signal.

In a first phase, the first switch may be closed-circuited based on the first control signal to transfer a first reference signal to the first input terminal and the second switch may be open-circuited based on the second control signal to transfer the first input signal to the second input terminal. In a second phase, the first switch may be open-circuited to transfer the first input signal to the first input terminal and the second switch may be closed-circuited based on the second control signal to transfer the first reference signal to the second input terminal.

A terminal of the first switch and a terminal of the second switch may be connected to a reference signal.

The first inputter may further include: a first capacitor connected to the first switch and the first input terminal; and a second capacitor connected to the second switch and the second input terminal.

The second inputter may include: a third switch of which a switching operation is controllable based on a third control signal; and a fourth switch of which a switching operation is controllable based on a fourth control signal that does not overlap the third control signal.

In a first phase, the third switch may be closed-circuited based on the third control signal to transfer a second reference signal to the third input terminal and the fourth switch may be open-circuited based on the fourth control signal to transfer the second input signal to the fourth input terminal. In a second phase, the third switch may be open-circuited based on the third control signal to transfer the second input signal to the third input terminal and the fourth switch may be closed-circuited based on the fourth control signal to transfer the second reference signal to the fourth input terminal.

The second inputter may further include: a third capacitor connected to the third switch and the third input terminal; and a fourth capacitor connected to the fourth switch and the fourth input terminal.

Other features and aspects will be apparent from the following detailed description, the drawings, and the claims.

BRIEF DESCRIPTION OF DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
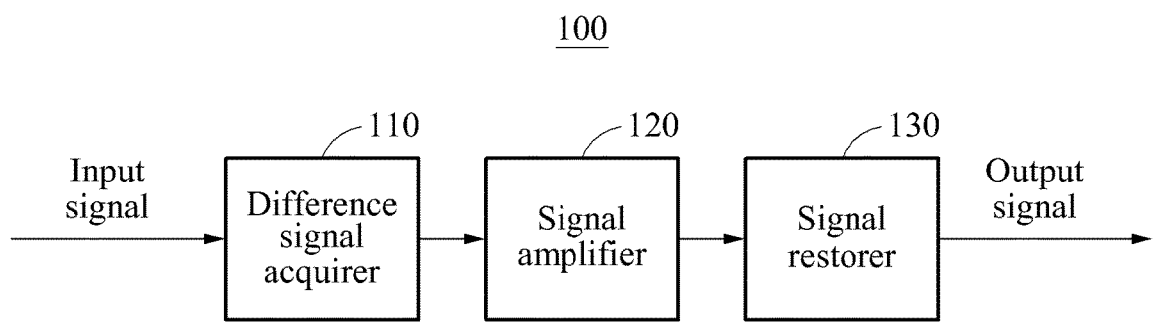
FIG. 1 is a diagram illustrating an example of a signal processing apparatus.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

The terminology used herein is for the purpose of describing particular examples only and is not to limit the examples. As used herein, terms such as first, second, A, B, (a), (b), and the like may be used herein to describe components. Each of these terminologies is not used to define an essence, order or sequence of a corresponding component but used merely to distinguish the corresponding component from other component(s).

It should be noted that if it is described in the disclosure that one component is "connected," "coupled," or "joined" to another component, a third component may be "connected," "coupled," and "joined" between the first and second components, although the first component may be directly connected, coupled or joined to the second component.

The singular forms "a," "an," and "the" are intended to include the plural forms as well, unless the context clearly indicates otherwise. As used herein, the terms "comprises," "comprising," "includes," "including," "has," and "having" specify the presence of stated features, numbers, operations, elements, components, and combinations thereof, but do not preclude the presence or addition of one or more other features, numbers, operations, elements, components, and combinations thereof.

Hereinafter, examples are described in detail with reference to the accompanying drawings. Like reference numerals in the drawings denote like elements, and a known function or configuration will be omitted herein.

FIG. 1 is a diagram illustrating an example of a signal processing apparatus 100. The signal processing apparatus 100 amplifies an input signal, for example, a biosignal, and outputs the amplified signal. The signal processing apparatus 100 obtains a difference signal of the input signal, amplifies the difference signal, and restores information of the original input signal from the amplified difference signal. Thus, the signal processing apparatus 100 enables measuring of an input signal having an amplitude range broader than a circuit operation amplitude range. Here, the difference signal is a signal reflecting changes in the amplitude of the input signal at a time interval. Hereinafter, functions and operations of the signal processing apparatus 100 will be described in more detail.

Referring to FIG. 1, the signal processing apparatus 100 includes a difference signal acquirer 110, a signal amplifier 120, and a signal restorer 130. The difference signal acquirer 110 obtains a difference signal from an input signal. The difference signal reflects a change in the input signal at a preset time interval based on a reference signal. The reference signal may be, for example, a bias voltage having a preset voltage value. In an example, the difference signal may be periodically set to be a signal value of the reference signal, and have a signal form reflecting the voltage change in the input signal, starting from the signal voltage value of the reference signal.

The difference signal acquirer 110 obtains the difference signal through a switching operation of a switch controlled by a control signal. Here, the switching operation refers to switching between a closed-circuit state and an open-circuit state of the switch. In an example, the difference signal acquirer 110 may periodically closed-circuit the switch to reset an input terminal of the signal amplifier 120 to be the reference signal, and then open-circuit the switch to obtain the difference signal reflecting the change in the input signal, or perform the switching in another manner. The switch may perform the switching operation in a period shorter than a period of the input signal. A process of obtaining a difference signal by the a difference signal acquirer, such as the difference signal acquirer 110, through a switching operation will be described in more detail with reference to FIGS. 4A and 4B.

The signal amplifier 120 amplifies the difference signal input from the difference signal acquirer 110 and outputs the amplified difference signal. In an example, a range in which an amplitude of the difference signal changes, or an amplitude change range of the difference signal, for example, a signal range, may be smaller than an amplitude change range of the input signal. This is the case because the difference signal is periodically reset to be the signal value of the reference signal, for example, a set voltage value. Thus, although an input signal deviating from a signal amplitude range that may be amplifiable by the signal amplifier 120 is input, the signal processing apparatus 100 may still perform normal amplification of the input signal because a corresponding difference signal having a reduced signal amplitude range is input to the signal amplifier 120.

The signal restorer 130 restores information about the original input signal based on the amplified difference signal output from the signal amplifier 120. In an example, the signal restorer 130 may generate an output signal by converting the amplified difference signal to a digital signal and summing, or accumulating, the digital signal corresponding to a period of the input signal obtained through the converting Here, the output signal corresponds to a signal obtained by amplifying an input signal of the signal processing apparatus 100 and converting the amplified signal to a digital signal. A signal restoring process performed by a signal restorer, such as the signal restorer 130, will be described in more detail with reference to FIGS. 2, 4A, and 4B.

In an example, the signal processing apparatus 100 may be applied to an amplifying circuit configured to amplify a measured signal and output the amplified signal. In general, when a signal having a signal amplitude range broader than an input amplitude range that the corresponding amplifying circuit is capable of receiving or is designed to receive, is input to an amplification terminal, saturation may occur at the amplification terminal and the signal may not be normally amplified. As described above, the signal processing apparatus 100 may convert a signal having a broad signal amplitude range to a signal having a smaller signal amplitude range and amplify the signal obtained through the converting, and thus may normally amplify an input signal and output the amplified signal although the input signal has a signal amplitude range that is broader than the input amplitude range of the amplifying circuit to which the input signal is provided.

In addition, the signal processing apparatus 100 may reduce power consumption by lowering an operating voltage of the amplifying circuit. In general, the power consumption of the amplifying circuit may be determined by the operating voltage of the amplifying circuit and a current consumed in the circuit. For example, when an amplitude change range of an input signal is 30 millivolts (mV) and an amplification factor of the input signal is a centuple, an operating voltage of 3 volts (V) or greater may be needed for a normal operation of the underlying amplifying circuit. However, according to examples, the input signal having the amplitude change range of 30 mV may be converted to a time-series difference signal having a change range of 5 mV or less, and the operating voltage of the amplifying circuit may be lowered to 0.5V because an amplified difference signal has an amplified signal range of 0.5V or less when the difference signal is amplified by a factor of 100 times. Due to such a lowering of the operating voltage of the circuit, the power consumption of the amplifying circuit may be reduced.

Further, an influence by a harmonic distortion may be reduced because the input signal changes to a signal having a small signal amplitude range, or a small swing, in an inputter (e.g., input circuit or input switch) of the amplifying circuit, and thus a complexity in designing the amplifying circuit may be reduced.

Further, user convenience may be improved because an initial stabilization time may be reduced in an area requiring the initial stabilization time for the input signal. For example, in a personal authentication using a biosignal such as electrocardiogram (ECG), measurement and authentication may need to be rapidly performed after the amplifying circuit and a signal source are connected. In general, when measuring a biosignal using a metal electrode, a measured biosignal may be stabilized to be in a processible amplitude range a few seconds after the metal electrode comes in contact with a body due to a polarization property of a metallic material. Here, due to such an amount of time used in an initial stabilization process of the biosignal, an amount of time for the authentication may increase. In an example, although the biosignal measured through the metal electrode has a range greater than the operation range of the amplifying circuit, signal processing for converting the biosignal to a signal within the operation amplitude range of the amplifying circuit may be performed, and thus the amount of time for the initial stabilization process may decrease, the amount of time for the authentication may also decrease, and user convenience may be improved.

Figure 2:
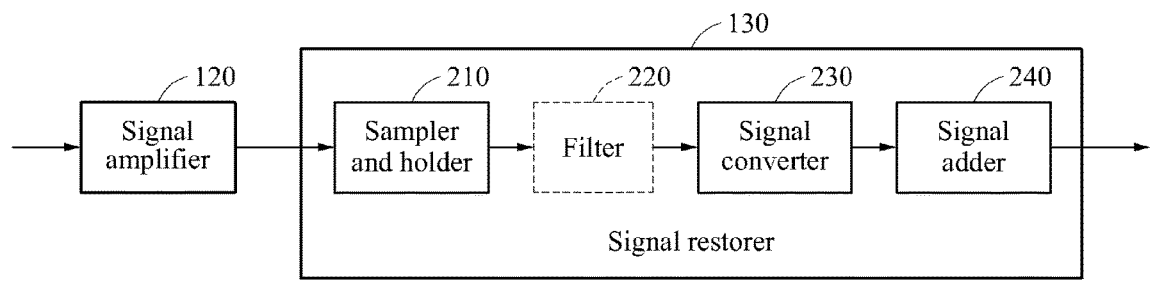
FIG. 2 is a diagram illustrating an example of a signal restorer.

FIG. 2 is a diagram illustrating an example of a signal restorer 130, according to an embodiment. Referring to FIG. 2, the signal restorer 130 includes a sampler and holder 210, a signal converter 230, and a signal adder 240, for example.

The sampler and holder 210 samples and holds a signal output from a signal amplifier 120. For example, the sampler and holder 210 may sample the signal output from the signal amplifier 120 using a switch and store the sampled signal in a storage, for example, a capacitor.

The signal converter 230 converts the signal sampled and held by the sampler and holder 210 to a signal in a digital domain. For example, the signal converter 230 may convert the signal output from the sampler and holder 210 to a digital signal using an analog-to-digital converter (ADC) configured to convert an analog signal to a digital signal.

The signal adder 240 generates an output signal by summing the digital signal corresponding to a period of the input signal output from the signal converter 230. The digital signal obtained through the converting by the signal converter 230 includes information associated with a change in an input signal, which is periodically obtained, and thus information about the original input is restored by adding the digital signal.

In another example, the signal restorer 130 further includes a filter 220. The filter 220 may reduce a high frequency noise component included in the signal sampled by the sampler and holder 210 by performing low-pass filtering on the sampled signal. The signal converter 230 converts the signal obtained through the low-pass filtering to a digital signal, and the signal adder 240 generates the output signal by adding the digital signal.

Figure 3A:
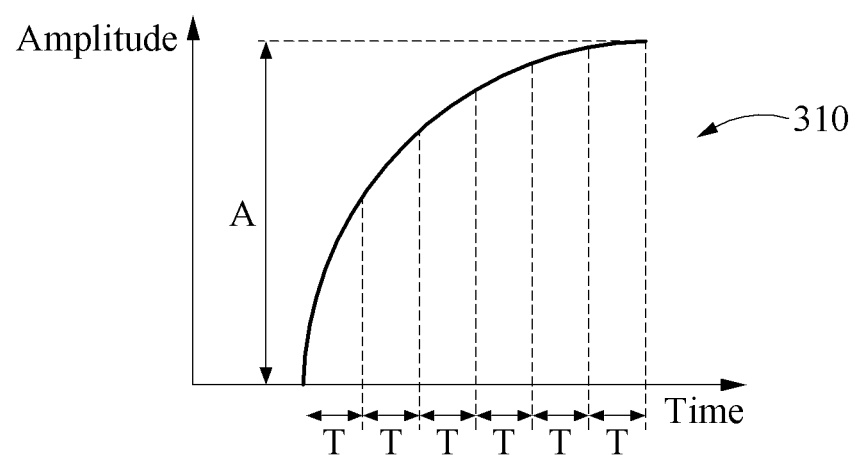
FIGS. 3A through 3D are diagrams illustrating an example of signal processing performed by a signal processing apparatus.
Figure 3B:
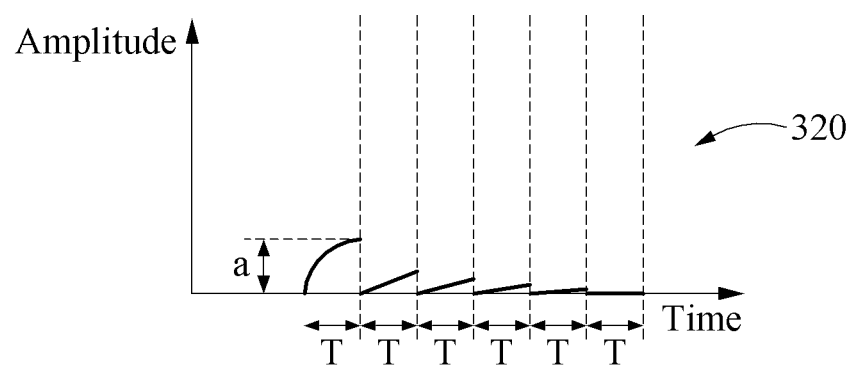

FIGS. 3A through 3D are diagrams illustrating an example of signal processing performed by a signal processing apparatus, according to one or more embodiments. In the example of FIG. 3A, "310" refers to an input signal input to the difference signal acquirer 110 of FIG. 1, and "A" refers to a signal amplitude range of the input signal 310 at a preset time interval, such as the illustrated six T intervals.

The difference signal acquirer 110 obtains a time-series difference signal from the input signal 310 through a switching operation performed in correspondence with each time interval T. The obtained difference signal is indicated as "320" in the example of FIG. 3B. The difference signal 320 is set to be a signal value of a reference signal at each time the difference signal 320 arrives at the beginning of each time interval T, and reflects a change in the amplitude of the input signal 310 after each time interval T after the difference signal 320 is set to be the signal value. Here, "a" indicates a maximum signal amplitude range of the difference signal 320.

Figure 3C:
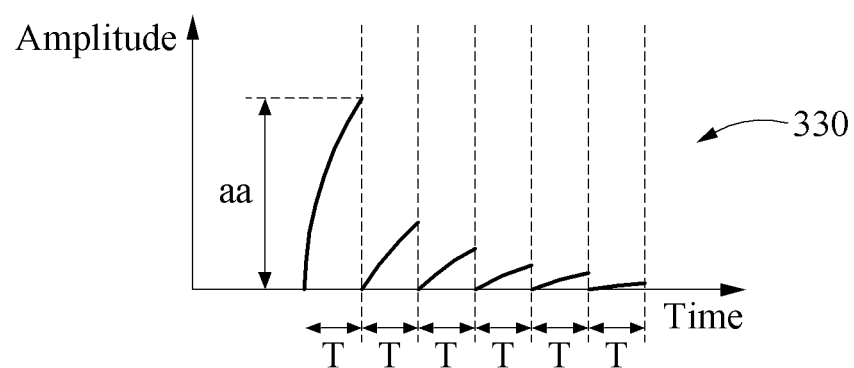

The difference signal 320 is amplified by the signal amplifier 120 of FIG. 1, for example, and, in the example of FIG. 3C, the amplified difference signal is indicated as "330," and "aa" indicates a maximum signal amplitude range of the amplified difference signal 330.

Figure 3D:
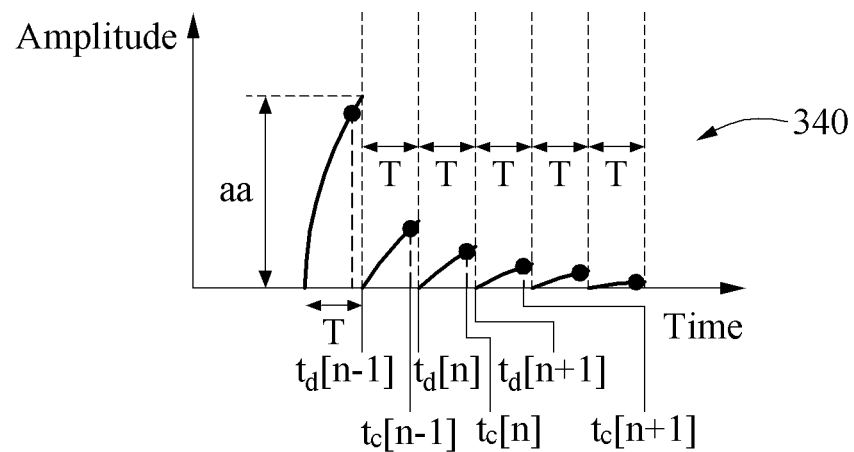

The amplified difference signal 330 is converted to a digital signal by the signal restorer 130 of FIG. 1. The digital signal obtained through the converting is indicated as "340," as shown in FIG. 3D. The signal restorer 130 samples the amplified difference signal 330 output from the signal amplifier 120 and converts a sampled value to a digital signal value, at a point in time before periodical difference is initiated by the difference signal acquirer 110. "$t_d[n-1]$," "$t_d[n]$," and "$t_d[n+1]$" indicate each point in time at which the periodical difference is initiated by the difference signal acquirer 110, and alternatively indicate a point in time at which an input terminal of the signal amplifier 120 is reset to be a signal value of a reference signal. "$t_c[n-1]$," "$t_c[n]$," and "$t_c[n+1]$" indicate each point in time at which analog-to-digital conversion is initiated by the signal restorer 130.

Figure 4A:
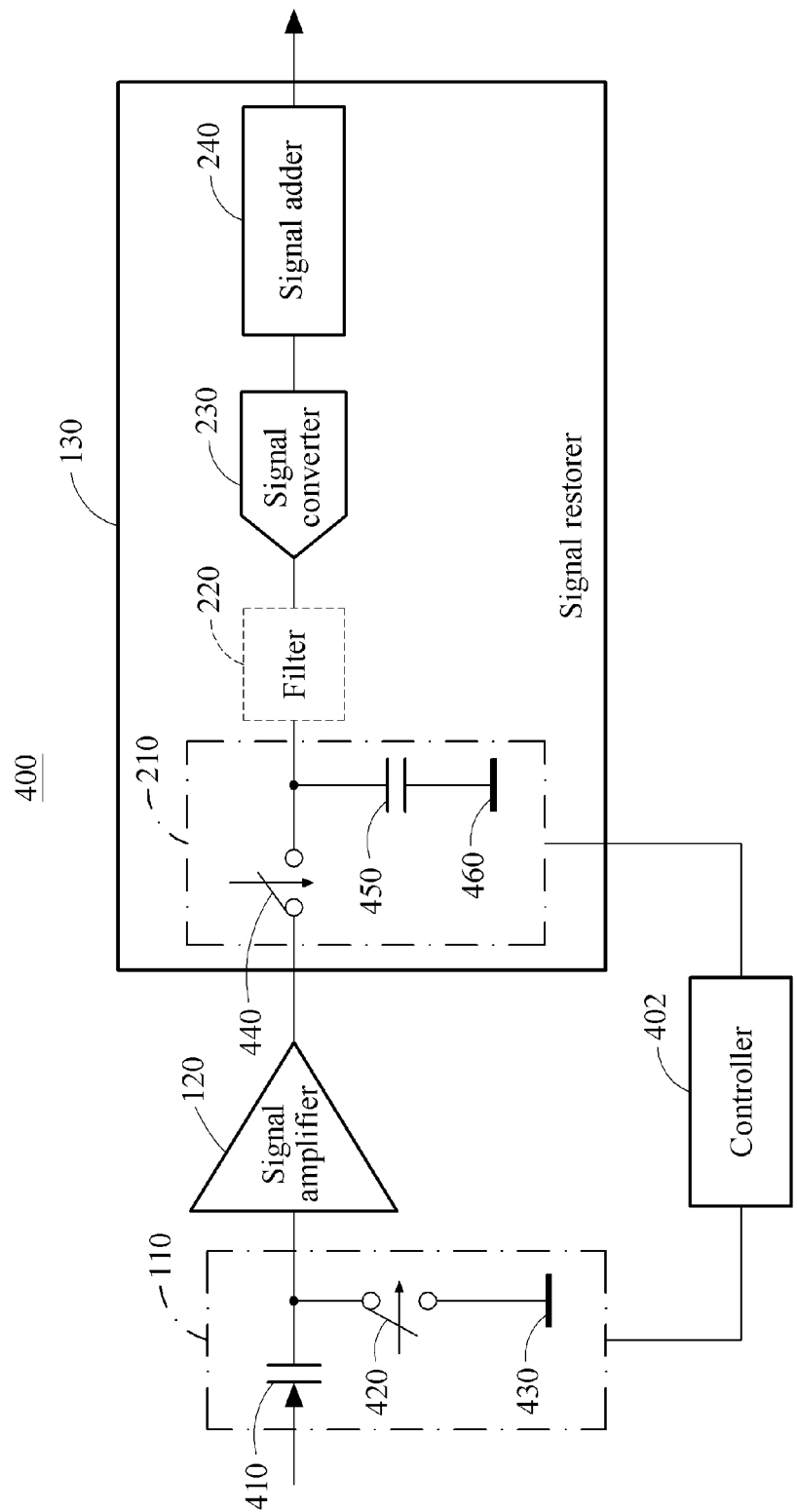
FIGS. 4A and 4B are diagrams illustrating examples of a circuit for implementing a signal processing apparatus.
Figure 4B:
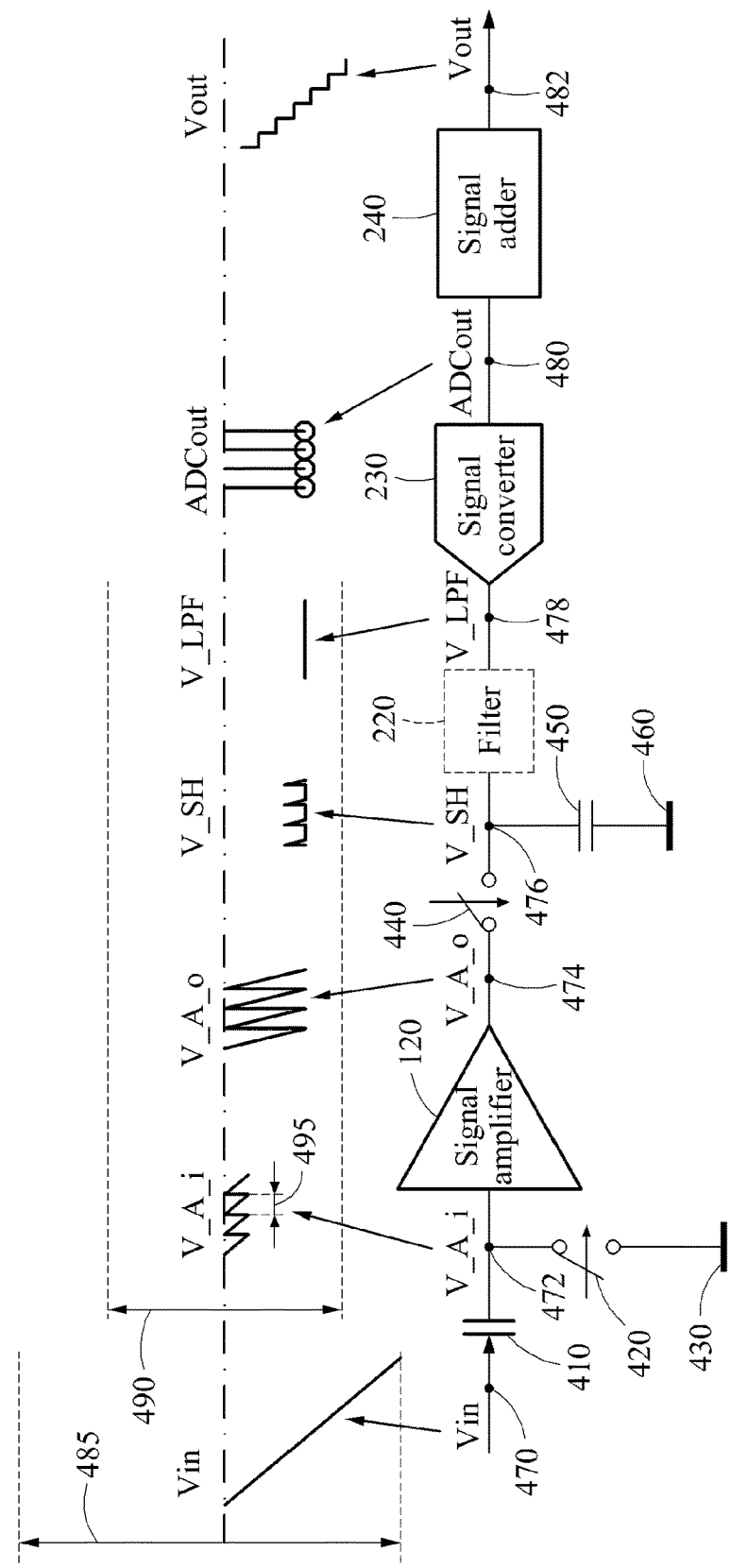

FIGS. 4A and 4B are diagrams illustrating examples of a circuit for implementing a signal processing apparatus 400, according to an embodiment. Referring to FIG. 4A, the signal processing apparatus 400 includes a difference signal acquirer 110, a signal amplifier 120, and a signal restorer 130, for example.

The difference signal acquirer 110 includes a first switch 420 and a first capacitor 410. A terminal of the first switch 420 is connected to an input terminal of the signal amplifier 120 and the first capacitor 410, and another terminal of the first switch 420 is connected to a first reference signal 430. A terminal of the first capacitor 410 is connected to the first switch 420 and the input terminal of the signal amplifier 120.

Each switching operation of the first switch 420 is controlled based on a first control signal, and performed in a shorter period of time than a period of an input signal, for example, a bandwidth of the input signal. In an example, the first control signal may control the first switch 420 to perform the switching operation in a period two or more times shorter than the period of the input signal.

In an open-circuit state of the first switch 420, the input signal passing through the first capacitor 410 is input to the signal amplifier 120. In a closed-circuit state of the first switch 420, the input terminal of the signal amplifier 120 is reset to be a signal value of the first reference signal 430, for example, a voltage value of a bias voltage. The first capacitor 410 disposed at a front end of the signal processing apparatus 400 removes an unnecessary direct current (DC) component from the input signal to prevent the DC component of the input signal from being transferred to the signal amplifier 120 and maintains the input terminal of the signal amplifier 120 to be the signal value of the first reference signal 430 in the closed-circuit state of the first switch 420.

After the closed-circuit state of the first switch 420 changes to the open-circuit state of the first switch 420, a signal to be input to the signal amplifier 120 may change as the input signal changes from a starting point, which is the signal value of the first reference signal 430. At each time the first switch 420 is closed-circuited, the input terminal of the signal amplifier 120 is set to be the signal value of the first reference signal 430 at that point in time, for example. When the first switch 420 is open-circuited, a signal reflecting the change in the input signal starting from the signal value of the first reference signal 430 is input to the signal amplifier 120. Through such a switching operation of the first switch 420, a difference signal reflecting the change in the input signal occurring at one or more time intervals during which the first switch 420 is closed-circuited is obtained.

The signal amplifier 120 amplifies the difference signal obtained by the difference signal acquirer 110. In an example, the input terminal of the signal amplifier 120 may be connected to a bias resistor (not shown) connected in parallel to the first switch 420 to set a reference bias of the signal amplifier 120.

As illustrated in FIG. 4A, a sampler and holder 210 includes a second switch 440 and a second capacitor 450. A terminal of the second switch 440 is connected to an output terminal of the signal amplifier 120, and another terminal of the second switch 440 is connected to the second capacitor 450 and a filter 220. A terminal of the second capacitor 450 is connected to the second switch 440 and the filter 220, and another terminal of the second capacitor 450 is connected to a second reference signal 460. In an example, the second reference signal 460 may selectively have a same signal value as the first reference signal 430.

The second switch 440 samples an output signal of the signal amplifier 120 based on a second control signal. The second capacitor 450 holds the signal sampled by the second switch 440. The second control signal may control the second switch 440 to sample the output signal of the signal amplifier 120 at a point in time before the first switch 420 is reset to a reference voltage, for example, immediately before the first switch 420 is closed-circuited.

The filter 220 performs low-pass filtering on a signal stored in the second capacitor 450, for example, the signal sampled by the second switch 440. The signal obtained through the low-pass filtering is converted to a digital signal by a signal converter 230. A signal adder 240 sums the digital signal corresponding to a period of the input signal (e.g., corresponding to all of the time intervals) obtained through the converting performed by the signal converter 230, to restore information of an original input signal.

In an example, the signal processing apparatus 400 may further include a controller 402 configured to generate the first and the second control signals, and control an overall operation of the signal processing apparatus 400.

FIG. 4B illustrates an example of a signal waveform measured at each node of the signal processing apparatus 400. Referring to FIG. 4B, an input signal Vin is input through a node 470, and a difference signal V_A_i is obtained through a switching operation of the first switch 420. A period 495 of the difference signal V_A_i is determined based on a period of the switching operation of the first switch 420 that is determined by the first control signal. The difference signal V_A_i is input through an input terminal 472 of the signal amplifier 120 and amplified by the signal amplifier 120, and the amplified difference signal V_A_o is output through an output terminal 474 of the signal amplifier 120.

The amplified difference signal V_A_o is sampled by the second switch 440, and the sampled signal V_SH is obtained at a node 476. The filter 220 performs low-pass filtering on the sampled signal V_SH, and the signal V_LPF obtained through the low-pass filtering is obtained at a node 478. The signal converter 230 converts the signal V_LPF to a digital signal ADCout through a digital sampling process, and the digital signal ADCout is obtained at a node 480. The signal adder 240 sums or builds the digital signal ADCout corresponding to the period of the input signal Vin to generate an output signal Vout, and the output signal Vout is output through an output terminal 482.

In the example of FIG. 4B, "485" indicates a signal voltage range of the input signal Vin, and "490" indicates an operation voltage range of a circuit to which the signal processing apparatus 400 is applied. As illustrated in FIG. 4B, although the input signal Vin having the signal voltage range 485 greater than the operation voltage range 490 of the circuit is input to the circuit, a normal amplification process may be performed as the difference signal V_A_i having a signal voltage range smaller than the signal voltage range 485 of the input signal Vin is amplified. As described in the foregoing, measurement of an input signal having a voltage range greater than an operation voltage range of a circuit may be enabled. Although a case in which a signal voltage range of an input signal is greater than an operation voltage range of a circuit is described herein, examples described herein are applicable to a case in which a signal voltage range of an input signal is within an operation voltage range of a circuit.

FIGS. 5A through 5D are diagrams illustrating examples of control signals to be applied to components of the signal processing apparatus 400 of FIG. 4A and examples of signals measured by the signal processing apparatus 400. In the examples of FIGS. 5A through 5D, "510" indicates a first control signal to be applied to the first switch 420 of FIG. 4A, "520" indicates a difference signal obtained by the difference signal acquirer 110 of FIG. 4A as an input signal of the signal amplifier 120 of FIG. 4A, "530" indicates an output signal of the signal amplifier 120, "540" indicates a second control signal to be applied to the second switch 440 of FIG. 4A, and "550" indicates an output signal of the sampler and holder 210 of FIG. 4A.

Figure 5A:
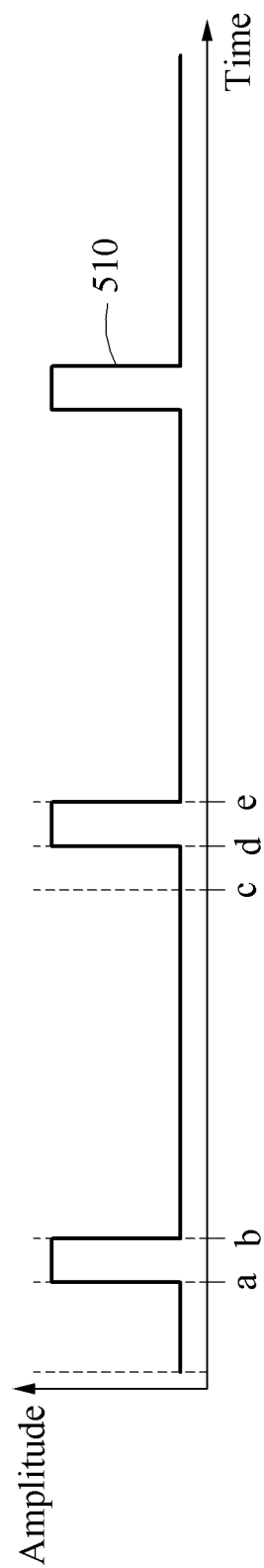
FIGS. 5A through 5D are diagrams illustrating examples of control signals to be applied to the signal processing apparatus of FIG. 4A and examples of signals measured by the signal processing apparatus of FIG. 4A.
Figure 5B:
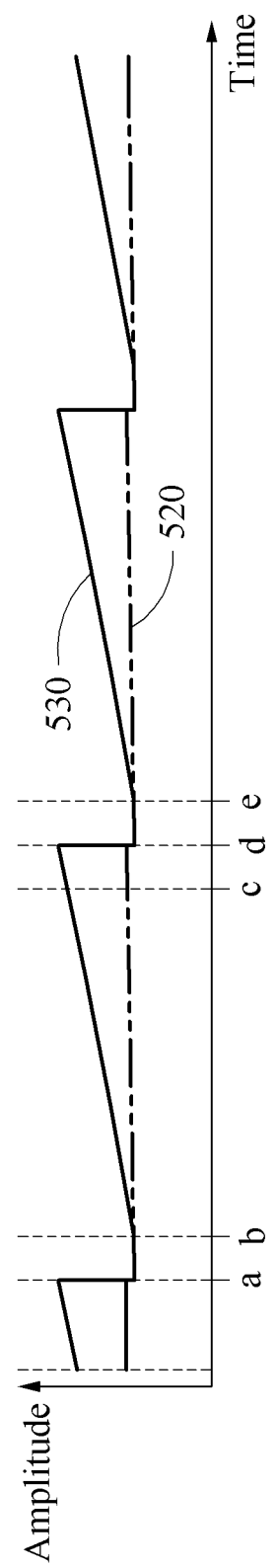

Referring to FIG. 5A, the first control signal 510 is controlled to be periodically at a logic high level. Referring to FIG. 5B, each time the first control signal 510 becomes logically high, the first switch 420 is closed-circuited and the input signal 520 of the signal amplifier 120 is set to be a signal value of a first reference signal 430. During a period of time in which the first control signal 510 is at the illustrated logic low level, the first switch 420 is open-circuited and a change in an input signal to be input to the signal processing apparatus 400 is reflected in the input signal 520 of the signal amplifier 120.

For example, as illustrated in FIGS. 5A and 5B, at a time interval between "a" and "b" and a time interval between "d" and "e," the first control signal 510 becomes logically high and the input signal 520 of the signal amplifier 120 is set to be the signal value of the first reference signal 430. Here, each of the interval between a and b and the interval between d and e may have a time length of 1 microsecond (μs), for example. At a time interval between "b" and "c" during which the first control signal 510 is logically low, the input signal 520 of the signal amplifier 120 may change as the input signal changes. As shown in FIG. 5B, the input signal 520 of the signal amplifier 120 is amplified by the signal amplifier 120, and the output signal 530 of the signal amplifier 120 is output.

Figure 5C:
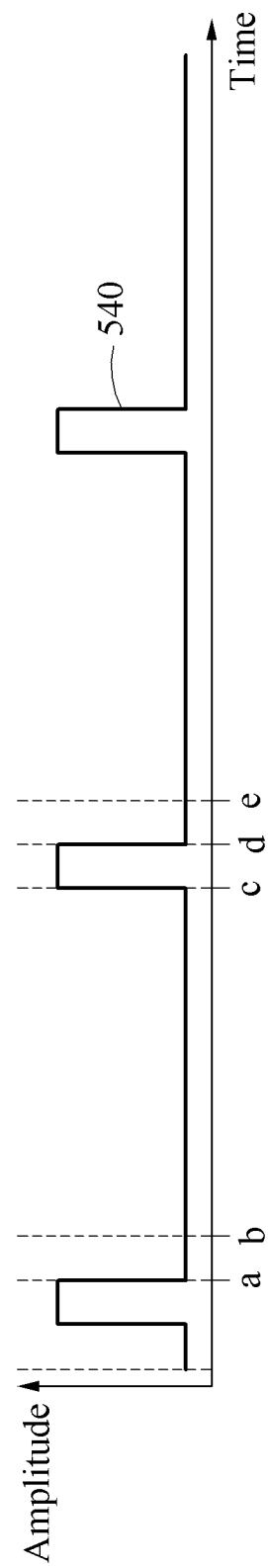

As shown in FIG. 5C, second control signal 540 is periodically at the illustrated logic high level at a point in time before the first control signal 510 becomes logically high. During a period of time in which the second control signal 540 is at the logic high level, the second switch 440 is closed-circuited and the output signal 530 of the signal amplifier 120 is sampled and held. During a period of time in which the second control signal 540 is at the illustrated logic low level, the second switch 440 is open-circuited and the output signal 550 of the sampler and holder 210 is maintained to have a sampled signal value of a previous time interval.

Figure 5D:
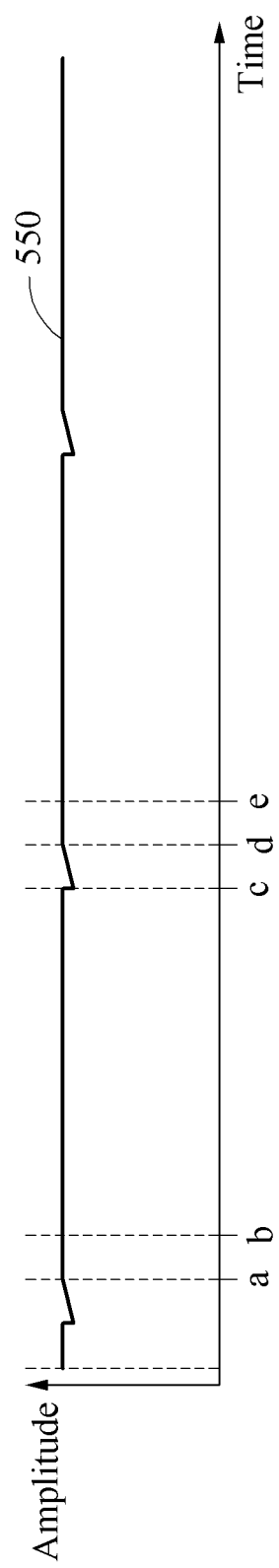

For example, as illustrated in FIG. 5D, at the time interval between "b" and "c," the second control signal 540 is illustrated as being logically low, and the output signal 550 of the sampler and holder 210 is maintained to have the sampled signal value of the previous time interval. At a time interval between "c" and "d," the second control signal 540 is logically high, and the output signal 550 of the sampler and holder 210 changes based on the output signal 530 of the signal amplifier 120.

Figure 6:
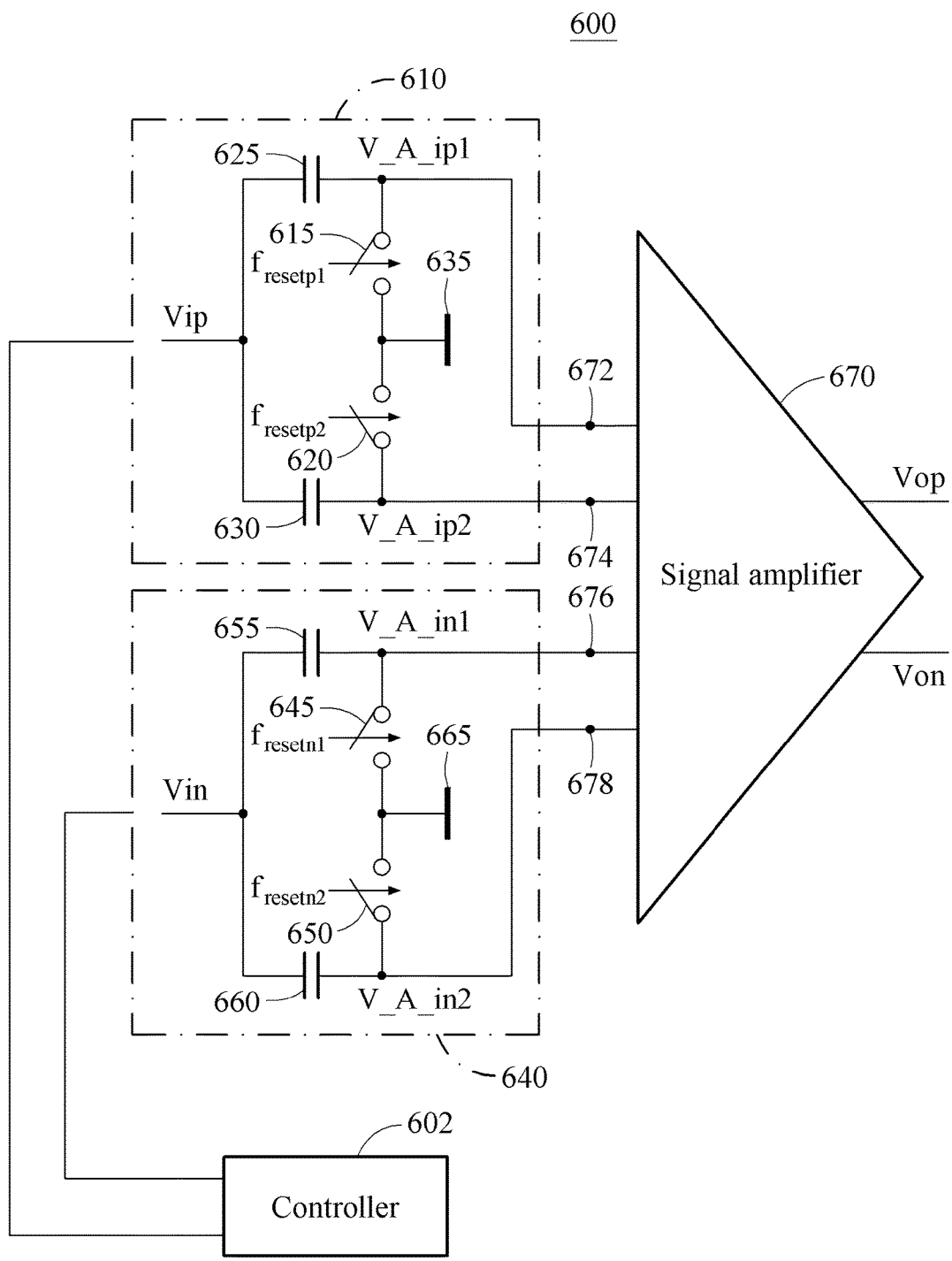
FIG. 6 is a diagram illustrating another example of a signal processing apparatus.

FIG. 6 is a diagram illustrating another example of a signal processing apparatus 600, according to an embodiment. In general, in a clock signal having periodicity, a rapid change may occur at a rising edge or a falling edge. In this case, when an input terminal of an amplifier is reset to be a reference signal at a time interval during which such a rising edge or a falling edge occurs, the amplifier may not normally amplify the clock signal.

In an example, the signal processing apparatus 600 applies an input signal to different input terminals of a signal amplifier 670 in different phases distinguished based on time, and thus may normally amplify the input signal having a form of a clock signal and increase a reset time of a switch for which an input terminal of the signal amplifier 670 is reset to have a signal value of a reference signal. Due to the increase in the reset time of the switch, use of a smaller-sized switch may be enabled.

As illustrated in FIG. 6, the signal processing apparatus 600 has a form of a differential dual input and a differential output. The term "differential dual input" indicates that the signal amplifier 670 has a form of a plus (+) input including two input terminals and a minus (−) input including two input terminals. The differential output indicates that the signal amplifier 670 has a form of a plus (+) output and a minus (−) output. However, a form of an input terminal and an output terminal of the signal amplifier 670 is not limited to the foregoing, and thus various modifications and changes may be made. Hereinafter, functions and operations of the signal processing apparatus, such as the signal processing apparatus 600 of FIG. 6, will be described in more detail based on a configuration of the signal processing apparatus 600, as only an example.

Referring to FIG. 6, the signal processing apparatus 600 includes a first input circuit or input switch (hereinafter, "inputter") 610 configured to transfer a first input signal Vip to the signal amplifier 670, a second input circuit or input switch (hereinafter, "inputter") 640 configured to transfer a second input signal Vin to the signal amplifier 670, and the signal amplifier 670. Here, the first input signal Vip and the second input signal Vin are in a relationship of a differential signal, and each of the signals has a form of a clock signal or at least periodic signals.

The first inputter 610 includes a first switch 615, a second switch 620, a first capacitor 625, and a second capacitor 630. A switching operation of each of the first switch 615 and the second switch 620 is controlled by a first control signal $f_{resetp1}$ and a second control signal $f_{resetp2}$, respectively.

A terminal of the first switch 615 is connected to the first capacitor 625 and a first input terminal 672 of the signal amplifier 670, and another terminal of the first switch 615 is connected to a first reference signal 635, for example, a bias voltage having a voltage value. A terminal of the first capacitor 625 is connected to the first switch 615 and the first input terminal 672 of the signal amplifier 670, and another terminal of the first capacitor 625 is connected to the first input signal Vip and the second capacitor 630. A terminal of the second switch 620 is connected to the second capacitor 630 and a second input terminal 674 of the signal amplifier 670, and another terminal of the second switch 620 is connected to the first reference signal 635. A terminal of the second capacitor 630 is connected to the second switch 620 and the second input terminal 674 of the signal amplifier 670, and another terminal of the second capacitor 630 is connected to the first input signal Vip and the first capacitor 625.

The first input terminal 672 and the second input terminal 674 of the signal amplifier 670 are connected to a first transistor and a second transistor, respectively, in the signal amplifier 670. In an example, both terminals of the first and the second transistors may be connected. For example, a drain terminal of the first transistor may be connected to a drain terminal of the second transistor, and a source terminal of the first transistor may be connected to a source terminal of the second transistor.

The first inputter 610 transfers the first input signal Vip alternately to the first input terminal 672 and the second input terminal 674. In an example, in a first phase, the first switch 615 is closed-circuited to transfer the first reference signal 635 to the first input terminal 672, and the second switch 620 is open-circuited to transfer the first input signal Vip to the second input terminal 674. In a second phase, the first switch 615 is open-circuited to transfer the first input signal Vip to the first input terminal 672, and the second switch 620 is closed-circuited to transfer the first reference signal 635 to the second input terminal 674. In each of the first and the second phases, a rising edge component and a falling edge component of the first input signal Vip may be transferred to the signal amplifier 670. The first inputter 610 may alternately and repetitively perform the first and the second phases.

The second inputter 640 includes a third switch 645, a fourth switch 650, a third capacitor 655, and a fourth capacitor 660. A switching operation of each of the third switch 645 and the fourth switch 650 is controlled by a third control signal $f_{resetn1}$ and a fourth control signal $f_{resetn2}$, respectively.

A terminal of the third switch 645 is connected to the third capacitor 655 and a third input terminal 676 of the signal amplifier 670, and another terminal of the third switch 645 is connected to a second reference signal 665. In an example, the second reference signal 665 may have a signal value equal to the signal value of the first reference signal 635. A terminal of the third capacitor 655 is connected to the third switch 645 and the third input terminal 676 of the signal amplifier 670, and another terminal of the third capacitor 655 is connected to the second input signal Vin and the fourth capacitor 660. A terminal of the fourth switch 650 is connected to the fourth capacitor 660 and a fourth input terminal 678 of the signal amplifier 670, and another terminal of the fourth switch 650 is connected to the second reference signal 665. A terminal of the fourth capacitor 660 is connected to the fourth switch 650 and the fourth input terminal 678 of the signal amplifier 670, and another terminal of the fourth capacitor 660 is connected to the second input signal Vin and the third capacitor 655.

The third input terminal 676 and the fourth input terminal 678 of the signal amplifier 670 are connected to a third transistor and a fourth transistor, respectively, in the signal amplifier 670. In an example, both terminals of the third transistor and the fourth transistor may be connected. For example, a drain terminal of the third transistor may be connected to a drain terminal of the fourth transistor, and a source terminal of the third transistor may be connected to a source terminal of the fourth transistor.

The second inputter 640 transfers the second input signal Vin alternately to the third input terminal 676 and the fourth input terminal 678. In an example, in a first phase, the third switch 645 is closed-circuited to transfer the second reference signal 665 to the third input terminal 676, and the fourth switch 650 is open-circuited to transfer the second input signal Vin to the fourth input terminal 678. In a second phase, the third switch 645 is open-circuited to transfer the second input signal Vin to the third input terminal 676, and the fourth switch 650 is closed-circuited to transfer the second reference signal 665 to the fourth input terminal 678. In each of the first and the second phases, a falling edge component and a rising edge component of the second input signal Vin may be transferred to the signal amplifier 670. The second inputter 640 may alternately and repetitively perform the first and the second phases.

The signal amplifier 670 amplifies difference signals of the first input signal Vip and the second input signal Vin and outputs the amplified difference signals. The difference signals output from the signal amplifier 670, for example, a difference signal Vop and a difference signal Von, may be restored in a digital domain. For example, the restoration may be performed by respectively sampling and converting the output signals of the signal amplifier 670 by an ADC, and using a method of adding a digital value obtained through the converting or performing integration on the digital value or a method of shifting a signal value at a time interval.

In an example, the signal processing apparatus 600 may further include a controller 602 configured to generate the first, the second, the third, and the fourth control signals and control an overall operation of the signal processing apparatus 600.

FIGS. 7A through 7D are diagrams illustrating examples of control signals generated by the controller and to be applied to the signal processing apparatus 600 of FIG. 6 and examples of signals measured by the signal processing apparatus 600.

Figure 7A:
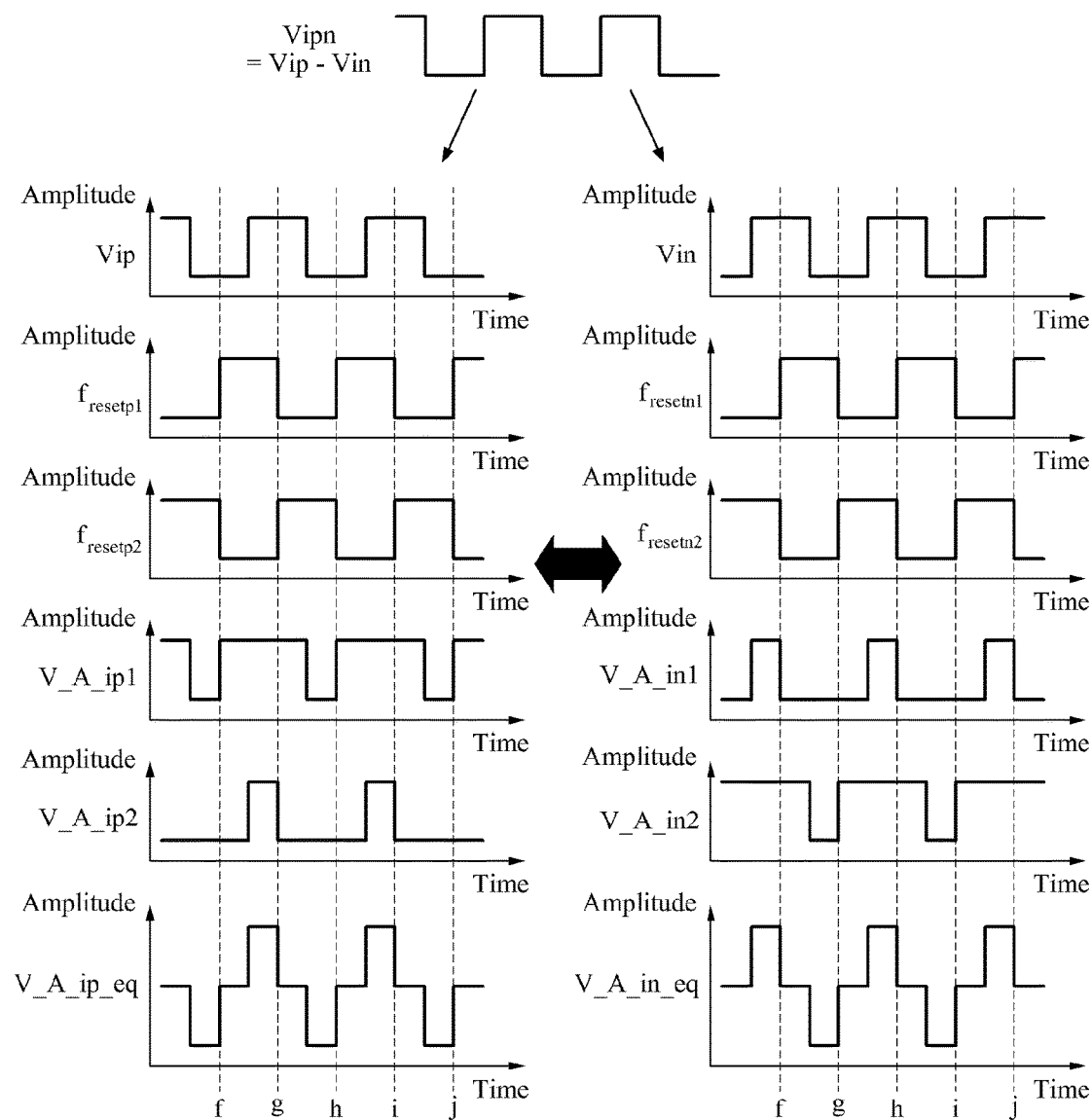
FIGS. 7A through 7D are diagrams illustrating examples of control signals to be applied to the signal processing apparatus of FIG. 6 and examples of signals measured by the signal processing apparatus of FIG. 6.

Referring to FIG. 7A, an input signal Vipn in a form of a clock signal is classified into a first input signal Vip and a second input signal Vin, which are in a relationship of a difference signal. The first input signal Vip and the second input signal Vin are input to the first inputter 610 and the second inputter 640, respectively.

The first control signal $f_{resetp1}$ is applied to the first switch 615, and the second control signal $f_{resetp2}$ is applied to the second switch 620. The first control signal $f_{resetp1}$ and the second control signal $f_{resetp2}$ are non-overlapping signals, and have opposite phases to each other. The first control signal $f_{resetp1}$ and the second control signal $f_{resetp2}$ may be at a logic high level when the first switch 615 and the second switch 620 are closed-circuited, for example.

For example, as illustrated in FIG. 7A, when the first control signal $f_{resetp1}$ is logically high, for example, at a time interval between "f" and "g" and a time interval between "h" and "i," the first reference signal 635 is input to the first input terminal 672. Here, the second control signal $f_{resetp2}$ is logically low, and the first input signal Vip is input to the second input terminal 674. A rising edge component of the first input signal Vip is input to the second input terminal 674, resulting in the amplified V_A_ip1 signal.

When the first control signal $f_{resetp1}$ is logically low, for example, at a time interval between "g" and "h" and a time interval between "i" and "j," the first input signal Vip is input to the first input terminal 672. Here, the second control signal $f_{resetp2}$ is logically high, and the first reference signal 635 is input to the second input terminal 674. A falling edge component of the first input signal Vip is input to the first input terminal 672 resulting in the amplified V_A_ip2 signal.

When the first input terminal 672 and the second input terminal 674 are connected to respective input transistors having the same influence on a back end of a circuit and both terminals of the input transistors are connected, a dual input signal to be input through the first input terminal 672 and the second input terminal 674 may be equivalent to an input of the illustrated V_A_ip_eq signal, from the back end of the circuit.

A process similar to the process performed on the first inputter 610 may be performed on the second inputter 640 to which the second input signal Vin is input. When the third control signal $f_{resetn1}$ is logically high, for example, at a time interval between "f" and "g" and a time interval between "h" and "i," the second reference signal 665 is input to the third input terminal 676. Here, the fourth control signal $f_{resetn2}$ is logically low, and the second input signal Vin is input to the fourth input terminal 678. A falling edge component of the second input signal Vin is input to the fourth input terminal 678, resulting in the amplified V_A_in1 signal.

When the third control signal $f_{resetn1}$ is logically low, for example, at a time interval between "g" and "h" and a time interval between "i" and "j," the second input signal Vin is input to the third input terminal 676. Here, the fourth control signal $f_{resetn2}$ is logically high, and the second reference signal 665 is input to the fourth input terminal 678. A rising edge component of the second input signal Vin is input to the third input terminal 676 resulting in the amplified V_A_in2 signal.

When the third first input terminal 676 and the fourth input terminal 678 are connected to respective input transistors having the same influence on the back end of the circuit and both terminals of the input transistors are connected, a dual input signal to be input through third input terminal 676 and the fourth input terminal 678 may be equivalent to an input of the illustrated V_A_in_eq signal, from the back end of the circuit.

Figure 7B:
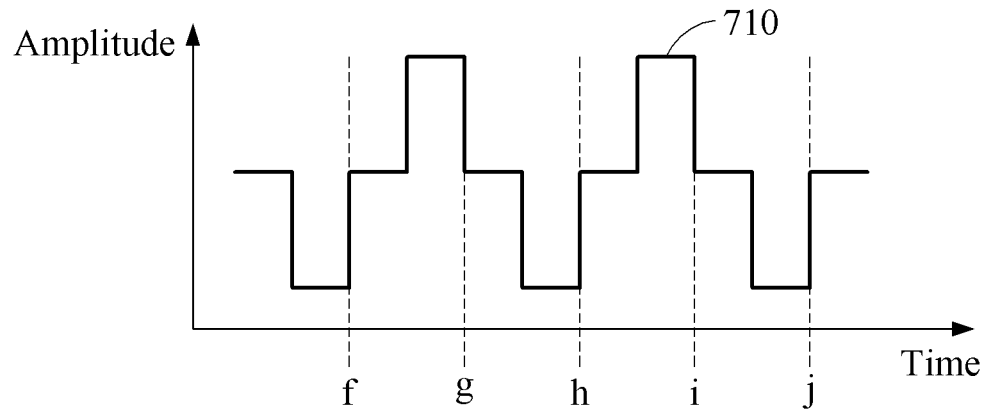
Figure 7C:
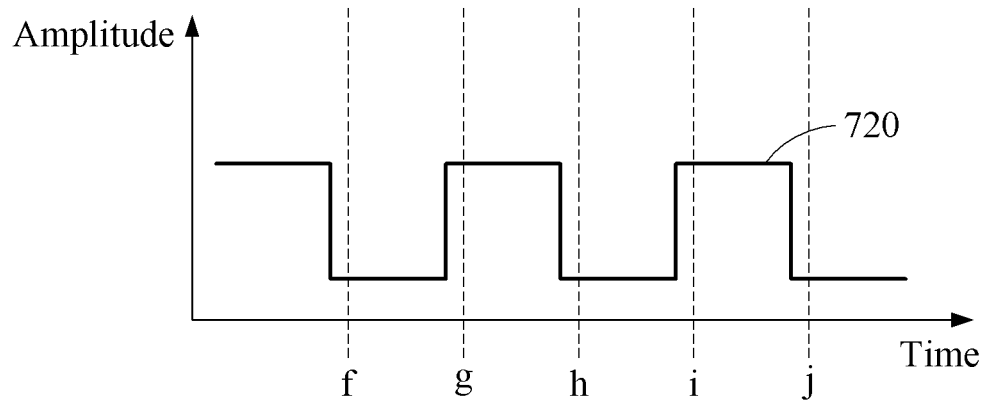
Figure 7D:
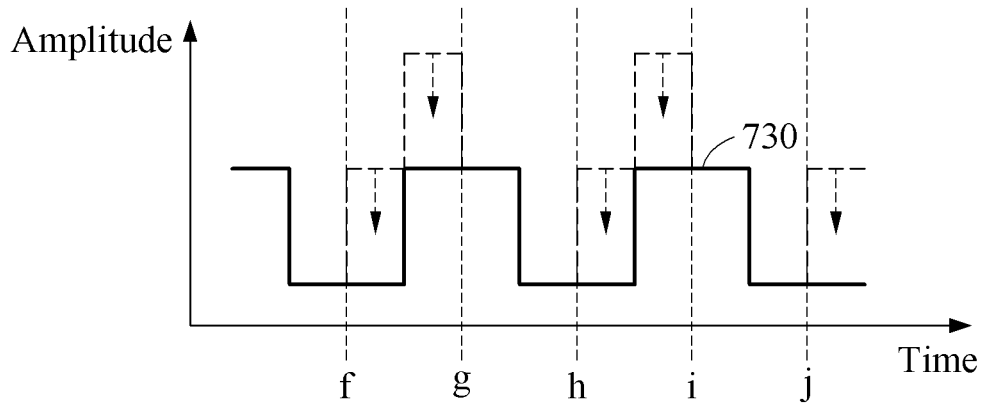

In FIG. 7B, "710" indicates a signal waveform obtained by subtracting a signal waveform of V_A_in_eq from a signal waveform of V_A_ip_eq, which are illustrated in FIG. 7A. A signal to be input through the first through fourth input terminals 672, 674, 676, and 678 of the signal amplifier 670 may be equivalent to an input of a signal having the signal waveform 710. The signal waveform 710 may be amplified by the signal amplifier 670, and information about an original input signal may be restored based on the amplified signal. For example, as shown in FIG. 7C, for the signal restoration, a method of sampling an output signal of the signal amplifier 670 at a point in time immediately before a point, for example, f, g, h, i, and j, and continuously adding a sampled value may be used. Here, a resulting signal waveform is indicated as "720." For another example, as shown in FIG. 7D, as indicated as "730," a signal may be restored using a method of shifting a signal value at a time interval, for example, simply shifting a signal value at a time interval between "f" and "g" and a time interval between "h" and "i."

Figure 8:
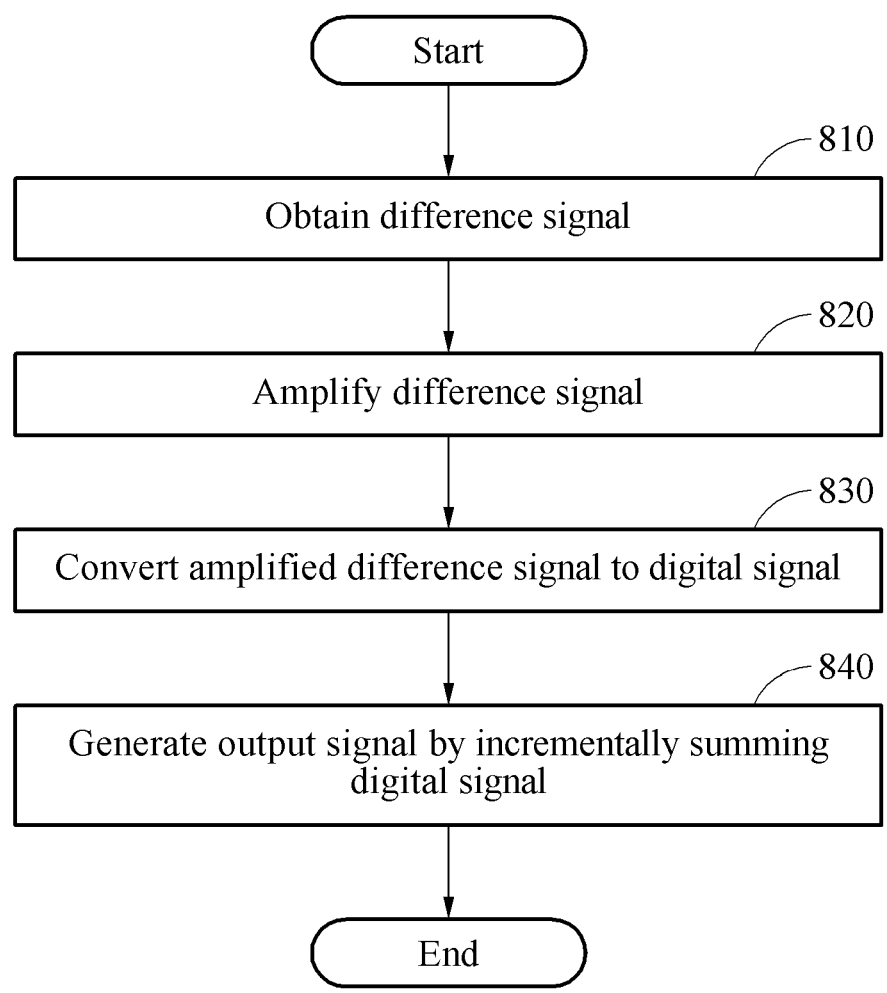
FIG. 8 is a flowchart illustrating an example of a signal processing method.

FIG. 8 is a flowchart illustrating an example of a signal processing method in accordance with an embodiment. The signal processing method may be performed by a signal processing apparatus, for example, the signal processing apparatus 100 of FIG. 1 and the signal processing apparatus 400 of FIG. 4A. Alternative implementations of a signal processing method are also possible.

Referring to FIG. 8, in operation 810, the signal processing apparatus obtains a difference signal of an input signal based on a switching operation. The signal processing apparatus may periodically closed-circuit a switch to reset an input terminal of a signal amplifier to be a reference signal, and then periodically open-circuit the switch to obtain the difference signal reflecting a change in the input signal. In operation 820, the signal processing apparatus amplifies the difference signal. In operation 830, the signal processing apparatus converts the amplified difference signal to a digital signal. The signal processing apparatus may sample the amplified difference signal based on the switching operation and convert the sampled signal to the digital signal. In operation 840, the signal processing apparatus generates an output signal by summing the digital signal. The signal processing apparatus may generate the output signal including information about an original input signal by summing or accumulating the digital signal based on time (e.g., corresponding to a period of a periodic input signal).

The apparatuses, units, modules, devices, and other components illustrated in FIGS. 1, 2, 4A, 4B, and 6 (e.g., the difference signal acquirer 110, signal amplifiers 120, 670 signal restorer 130, sampler and holder 210, filter 220, signal converter 230, signal adder 240 and signal inputters 610, 640) that perform the operations described herein with respect to FIG. 8 are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIG. 8. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The method illustrated in FIG. 8 that performs the operations described herein with respect to FIGS. 1, 2, 4A, 4B, and 6 is performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A signal processing apparatus, comprising:
   a signal amplifier comprising a first input terminal, a second input terminal, a third input terminal and a fourth input terminal;
   a first inputter configured to transfer a first input signal alternately to the first input terminal and the second input terminal;
   a second inputter configured to transfer a second input signal alternately to the third input terminal and the fourth input terminal,
   wherein the signal amplifier is configured to amplify a difference signal based on the first input signal and the second input signal, and output the amplified difference signal; and
   a signal restorer configured to convert the amplified difference signal to a digital signal and integrate the digital signal over preset time intervals.

2. The apparatus of claim 1, wherein the first inputter comprises:
   a first switch of which a switching operation is controllable based on a first control signal; and
   a second switch of which a switching operation is controllable based on a second control signal.

3. The apparatus of claim 2, wherein:
   in a first phase, the first switch is close-circuited based on the first control signal to transfer a first reference signal to the first input terminal and the second switch is open-circuited based on the second control signal to transfer the first input signal to the second input terminal; and
   in a second phase, the first switch is open-circuited based on the first control signal to transfer the first input signal to the first input terminal and the second switch is close-circuited based on the second control signal to transfer the first reference signal to the second input terminal.

4. The apparatus of claim 2, wherein a terminal of the first switch and a terminal of the second switch are connected to a reference signal.

5. The apparatus of claim 2, wherein the first inputter further comprises:
- a first capacitor connected to the first switch and the first input terminal; and
- a second capacitor connected to the second switch and the second input terminal.

6. The apparatus of claim 2, wherein the second inputter comprises:
- a third switch of which a switching operation is controllable based on a third control signal; and
- a fourth switch of which a switching operation is controllable based on a fourth control signal that does not overlap the third control signal.

7. The apparatus of claim 6, wherein:
in a first phase, the third switch is close-circuited based on the third control signal to transfer a second reference signal to the third input terminal and the fourth switch is open-circuited based on the fourth control signal to transfer the second input signal to the fourth input terminal; and
in a second phase, the third switch is open-circuited based on the third control signal to transfer the second input signal to the third input terminal and the fourth switch is close-circuited based on the fourth control signal to transfer the second reference signal to the fourth input terminal.

8. The apparatus of claim 6, wherein the second inputter further comprises:
- a third capacitor connected to the third switch and the third input terminal; and
- a fourth capacitor connected to the fourth switch and the fourth input terminal.

9. The apparatus of claim 1, wherein the signal restorer is configured to generate an output signal reflecting at least one of the first input signal and the second input signal, based on the integrating.

10. The apparatus of claim 1, wherein, for the integrating over the time intervals, the signal restorer is configured to incrementally integrate a digital signal of a current time to an integrated digital signal of a previous time.

11. A signal processing apparatus, comprising:
- a signal amplifier comprising a first input terminal, a second input terminal, a third input terminal and a fourth input terminal;
- a first inputter configured to transfer a first input signal alternately to the first input terminal and the second input terminal;
- a second inputter configured to transfer a second input signal alternately to the third input terminal and the fourth input terminal,
wherein the signal amplifier is configured to amplify a difference signal based on the first input signal and the second input signal, and output the amplified difference signal; and
- a signal restorer configured to convert the amplified difference signal to a digital signal and incrementally sum a digital signal of a current time to a summed digital signal of a previous time.

* * * * *